(12) United States Patent
Kim et al.

(10) Patent No.: US 10,987,447 B2
(45) Date of Patent: Apr. 27, 2021

(54) ANTIBACTERIAL DRESSING MATERIAL AND PREPARING METHOD THEREFOR

(71) Applicant: GENEWEL CO., LTD., Gyeonggi-do (KR)

(72) Inventors: Hyun Jung Kim, Gyeonggi-do (KR); Il Kyu Park, Gyeonggi-do (KR); Seung Moon Lee, Gyeonggi-do (KR); Yong Soo Kim, Daejeon (KR)

(73) Assignee: Genewel Co., Ltd., Gyeonggi-Do (KR)

( * ) Notice: Subject to any disclaimer, the term of this patent is extended or adjusted under 35 U.S.C. 154(b) by 382 days.

(21) Appl. No.: 15/750,647

(22) PCT Filed: Mar. 25, 2016

(86) PCT No.: PCT/KR2016/003071
§ 371 (c)(1),
(2) Date: Feb. 6, 2018

(87) PCT Pub. No.: WO2017/026618
PCT Pub. Date: Feb. 16, 2017

(65) Prior Publication Data
US 2020/0093953 A1    Mar. 26, 2020

(30) Foreign Application Priority Data
Aug. 12, 2015 (KR) .................. 10-2015-0113661

(51) Int. Cl.
*A61L 15/26* (2006.01)
*A61L 15/44* (2006.01)
*A61L 15/46* (2006.01)
*A61L 15/16* (2006.01)

(52) U.S. Cl.
CPC .............. *A61L 15/46* (2013.01); *A61L 15/16* (2013.01); *A61L 15/26* (2013.01); *A61L 15/44* (2013.01)

(58) Field of Classification Search
CPC ...................................................... A61L 15/16
See application file for complete search history.

(56) References Cited

U.S. PATENT DOCUMENTS

| | | | |
|---|---|---|---|
| 5,445,604 A | 8/1995 | Lang et al. | |
| 2004/0018227 A1* | 1/2004 | Park ................. | A61F 13/00991 424/445 |
| 2007/0122463 A1* | 5/2007 | Ko .......................... | A61K 33/24 424/445 |
| 2008/0146983 A1* | 6/2008 | Park ................. | A61F 13/00034 602/46 |

FOREIGN PATENT DOCUMENTS

| | | |
|---|---|---|
| JP | 57-153644 A | 9/1982 |
| JP | 2007-144149 A | 6/2007 |
| JP | 2008-149103 A | 7/2008 |
| KR | 10-2002-0046619 A | 6/2002 |
| KR | 10-2008-0060213 A | 7/2008 |
| KR | 20-2010-0009549 U | 9/2010 |
| KR | 10-1199453 B1 | 11/2012 |
| KR | 10-2014-0107694 A | 9/2014 |
| KR | 10-2015-0041047 A | 4/2015 |

OTHER PUBLICATIONS

International Search Report issued in PCT/KR2016/003071, dated Jun. 21, 2016.
Extended European Search Report issued in PCT/KR2016/003071, dated Apr. 5, 2019.

* cited by examiner

*Primary Examiner* — Gina C Justice
(74) *Attorney, Agent, or Firm* — Adsero IP (57) ABSTRACT

The present invention relates to an antibacterial dressing and a method for preparing the same. According to the present invention, there are provided an antibacterial dressing containing a rapid cell membrane-penetrating component that exhibits excellent bactericidal and antibacterial activities by disrupting the structure and synthesis of protein and nucleic acid, and a method for preparing the same.

16 Claims, 8 Drawing Sheets

ANTIBACTERIAL DRESSING MATERIAL AND PREPARING METHOD THEREFOR

RELATED APPLICATIONS

This application is a National Stage Entry of International Application No. PCT/KR2016/003071, filed on Mar. 25, 2016, and claims the benefit of Korean Application No. 10-2015-0113661, filed on Aug. 12, 2015, each of which is hereby incorporated by reference in its entirety for all purposes as if fully set forth herein.

TECHNICAL FIELD

The present invention relates to an antibacterial dressing and a method for preparing the same, and more particularly to an antibacterial dressing containing a rapid. cell membrane-penetrating component that exhibits excellent bactericidal and antibacterial activities by disrupting the structure and synthesis of protein. and nucleic acid, and to a method for preparing the same.

BACKGROUND ART

When a wound is created in the skin, the wound is healed through the inflammatory phase in which a large amount of wound exudate is produced, the proliferative phase in which granulation occurs in earnest, and then the maturation phase in which formation and remodeling of new tissue takes place. For wound healing, it is most preferable to use a non-adhesive dressing which minimizes the inflammatory phase by rapidly absorbing wound exudate, maintains a suitable moist environment to provide various cell growth factors (PDGF, TGF-β, EFG, FGF, VEGE, IGF, etc.) or cytokines (IL-1, IL-6, IL-8, TNF, etc.) that facilitate cell migration and proliferation to promote wound healing, and is easily removed from the wound surface upon replacement.

Examples of occlusive dressings that are currently mainly used include film type, hydrocolloid type, hydrogel type and polyurethane foam type dressings, etc. In particular, dressings having high therapeutic effects include hydrocolloid type, hydrogel type and polyurethane foam type dressings, etc.

Hydrocolloid type dressings disclosed in U.S. Pat. Nos. 5,503,847 and 5,830,932 comprise: an adhesive composition layer; a hydrocolloid layer that reduces external impact and absorbs exudate; and a film layer that prevents the penetration of bacteria and foreign matter.

These hydrocolloid type dressings form a gel by absorbing a small amount of wound exudate, provide a moist environment, and provide an environment that maintains pH at weakly acidic pH levels for a long period of time so as to prevent tissue damage and promote cell growth. However, these dressings have disadvantages in that they have insufficient moisture permeability and exudate absorption ability, and in that the gel attached to the wound surface remains as residue upon replacement or removal such that secondary removal operation is required, and also in that they are not suitable for application to wounds with a large amount of wound exudate.

In addition, hydrophilic polyurethane foam dressings disclosed in U.S. Pat. Nos. 5,445,604 and 5,065,752 have a three-layer structure comprising a film laminated on both sides of polyurethane foam. In these dressings, holes are mechanically formed in a wound contact layer film for preventing the macropores of a wound contact layer from adhering to the wound surface so that exudate is absorbed into the wound contact layer. However, these dressings have problems in that exudates and blood are not completely removed and blood clots are formed on the wound surface and act as a foreign body during treatment so as to delay wound healing or remain adhered to the wound surface due to blood coagulation upon removal, and in that adhesion of newly formed tissue occurs due to the mechanically formed macropores upon replacement of the dressings or the wound area has a dot shape which is not smooth. In addition, these dressings have problems in that when they are applied to wounds with a large amount of exudate, they need to be replaced frequently because their exudate absorption ability per unit area is insufficient, and also in that these dressings have an insufficient ability to retain exudate so that exudate readily leaks from the dressings ay external forces so as to stain the patient's clothes or sheets and dry the edge of the wound surface and dry the wound surface in wounds with a small amount of exudate (J Koeran Soc. Blast. Reconstr. Sur., Vol.29, No.4, 297-301, 2002; J Koeran Burn Soc., Vol.6, No. 1, 45-51, 2003).

Accordingly, there is still a need to develop a. foam-type dressing which has the capability to absorb a large amount of exudate, does not leak exudate after absorption, does not cause wound drying and contamination, is easily removed from a wound area without damaging newly formed tissue, is not toxic, and can protect the wound from external infection.

DISCLOSURE

Technical Problem

The present invention has been made in order to solve the above-described problems occurring in the prior art, and it is an object of the present invention to provide an antibacterial dressing which comprises a rapid cell membrane-penetrating component that exhibits excellent bactericidal and antibacterial activities by disrupting the structure and synthesis of protein and nucleic acid, and at the same time, is not toxic to cells, and a method for preparing the same.

Technical Solution

To achieve the above object, the present invention provides an antibacterial dressing comprising: an external infectious agent-blocking layer; a bacterial growth-inhibiting layer; and a wound infection agent-removing layer, the antibacterial dressing containing a rapid cell membrane-penetrating component.

The present invention also provides a method for preparing the antibacterial dressing, comprising preparing the antibacterial dressing using a continuous preparation apparatus.

Advantageous Effects

According to the present invention, there are provided an antibacterial dressing which comprises a rapid cell membrane-penetrating component that exhibits excellent bactericidal and antibacterial activities by disrupting the structure and synthesis of protein and nucleic acid, and a method for preparing the same.

DESCRIPTION OF DRAWINGS

4 depicts micrographs showing the results of cytotoxicity tests for Example 1 and Comparative Examples 1 to 3.

BEST MODE

Hereinafter, the present invention will be described in retail.

An antibacterial dressing according to the present invention comprises an external infectious agent-blocking layer, a bacterial growth-inhibiting layer, and a wound infection agent-removing layer, and is characterized by comprising a rapid cell membrane-penetrating component.

The term "external infectious agent-blocking layer", unless otherwise specified, refers to the uppermost layer of the dressing, which can prevent infection caused by invasion of external foreign substances and enables absorbed exudate to be released. externally with proper moisture permeability.

The term "bacterial growth-inhibiting layer", unless otherwise specified, refers to a layer which retains an antibacterial agent, slowly releases the antibacterial agent in a controlled manner, inhibits bacterial growth in a moisture environment, and has the ability to absorb and retain exudate.

The term "wound infection agent-removing layer", unless other specified, refers to a layer that prevents colony formation to remove infectious microorganisms, has an antibacterial effect, performs a barrier function, and does not adhere to the wound surface.

The term "rapid cell membrane-penetrating component", unless otherwise specified, refers to a component capable of rapidly penetrating the cell membrane so as to disrupt the structure and synthesis of protein and nucleic acid.

The antibacterial dressing of the present invention has an antibacterial activity of 99% or more as measured in accordance with ASTM E2149-10.

Furthermore, the antibacterial dressing of the present invention shows a cell viability of 80% or more, 85% or more, or 90% or more, as measured by a cytotoxicity test in accordance with ISO 10993-5, 12.

In addition, the antibacterial dressing of the present invention has an absorption capacity of 1.0 $g/cm^2$ or more as calculated using the following equation 1:

$$\text{Absorption capacity (g/cm}^2\text{)}=(W2-W1)g/\text{initial sample area (cm}^2\text{)} \quad \text{Equation 1}$$

wherein W1 is the initial weight of the dressing, measured after cutting the dressing to a size of 5 cm×5 cm and drying the cut dressing in a vacuum oven at 50° C. for 24 hours, and W2 is the weight of the dressing, measured after immersing the dressing in distilled water at 37° C. for 30 minutes and then removing water from the surface of the dressing.

Moreover, the antibacterial dressing of the present invention has a retaining capacity of 0.2 $g/cm^2$ or more as calculated using the following equation 2:

$$\text{Retaining capacity (g/cm}^2\text{)}=(W3-W1)g/\text{initial sample area (cm}^2\text{)} \quad \text{Equation 2}$$

wherein W1 is the initial weight of the dressing, measured after cutting the dressing to a size of 5 cm×5 cm and drying the cut dressing in a vacuum oven at 50° C. for 24 hours, and W3 is the weight of the dressing, measured after immersing the dressing in distilled water at 37° C. for 30 minutes, and then removing water from the surface of the dressing, and then pressing the dressing with a 5 kg weight for 20 minutes.

Furthermore, the antibacterial dressing of the present invention shows a re-epithelialization rate of 15% or more, 20 to 100%, 20 to 80%, or 20 to 50%, as calculated using the following equation 4, and shows an excellent skin regeneration effect in this range:

$$\text{Re-epithelialization rate (\%)}=\text{re-epithelialized length}/\text{initial wound length}*100 \quad \text{Equation 4}$$

The re-epithelialized length and the initial wound length are measured by shaving the entire back of SD (Sprague Dawley) rats, removing up to fascia layers in the center of the back to induce a 2.5 $cm^2$ wound, suturing the wound edges with a suture using a silicone ring in order to prevent wound contraction, applying the dressing to the wound, wrapping the dressing once with a self-adhesive bandage, fixing it with a sticking plaster, replacing the bandage at 3-day intervals, sacrificing the animal on day 14, collecting regenerated tissue, and performing tissue staining.

In addition, the antibacterial dressing of the present invention may show a newly formed blood vessel number of, for example, 60/2.5 $cm^2$ or more, 65 to 90/2.5 $cm^2$, or 65 to 80/2.5 $cm^2$, and shows an excellent skin regeneration effect in this range.

The newly formed blood vessel number is measured by shaving the entire back of SD (Sprague Dawley) rats, removing up to fascia layers in the center of the back to induce a 2.5 $cm^2$ wound, suturing the wound edges with a suture using a silicone ring in order to prevent window shrinkage, applying the dressing to the wound, wrapping the dressing once with a self-adhesive bandage, fixing it with a sticking plaster, replacing the bandage at 3-day intervals, sacrificing the animal on day 14, collecting regenerated.

tissue, performing tissue staining, and counting the blood vessel number of re-epithelialized tissue in a wound area of 2.5 cm².

In addition, the antibacterial dressing of the present invention may show a collagen deposition rate of, for example, 45% or more, 50 to 75%, or 55 to 70%, as calculated using the following equation 5, and shows an excellent skin regeneration effect in this range:

Collagen deposition rate (%)=collagen area of dermal layer/total area of dermal layer*100    Equation 5

The collagen deposition rate is measured by shaving the entire back of SD (Sprague Dawley) rats, removing up to fascia layers in the center of the back to induce a 2.5 cm² wound, suturing the wound edges with a suture using a silicone ring in order to prevent window shrinkage, applying the dressing to the wound, wrapping the wound once with a self-adhesive bandage, fixing it with a sticking plaster, replacing the bandage at 3-day intervals, sacrificing the animal on day 14, collecting regenerated tissue, performing special staining of dermal connective tissue collagen by Masson's trichrome staining, and measuring the area of collagen relative to the total area of three positions of the dermal layer by use of Image J program.

The rapid cell membrane-penetrating component may be, for example, an iodine compound. In another example, the rapid cell membrane-penetrating component is one or more selected from the group consisting of potassium, iodate, potassium biiodate, methyl iodide, hydroiodic acid, acetyl iodide, and Povidone iodine.

In another example, the rapid cell membrane-penetrating component may be a substance represented by the following formula 1:

Formula 1 wherein n is an integer ranging from 1 to 100, m is an integer ranging from 1 to 2000, and n m is 1:10 to 1:25.

n may be, for example, an integer ranging from 1 to 100, or an integer ranging from 10 to 80.

m may be, for example, as integer ranging from 1 to 2000, or an integer ranging from 1 to 1440.

m may be, for example, 1:10 to 1:25, preferably 1:15 to 1:20.

In one example, the bacterial growth-inhibiting layer and the wound infection agent-removing layer may contain. the rapid cell membrane-penetrating component. The rapid cell membrane-penetrating component is present in a uniformly dispersed form in the bacterial growth-inhibiting layer and the wound infection agent-removing layer. The bacterial growth-inhibiting layer and the wound infection agent-removing layer may contain the rapid cell membrane-penetrating component in an amount of, for example, 0.01 to 10 wt %, or 0.1 to 7 wt %, based on 100 wt % of the bacterial growth-inhibiting layer and the wound infection agent-removing layer, and shows excellent bactericidal and antibacterial activities in this range.

The bacterial growth-inhibiting layer may have a pore size of, for example, 500 μm or less, 0.01 to 400 μm, or 70 to 400 μm, and shows increased retaining ability in this range.

The expression "size of pores in the bacterial growth-inhibiting layer is 500 μm or less" may mean that the size of 80% or more, 90% or more or all of pores in the bacterial growth-inhibiting layer is 500 μm or less.

In addition, the bacterial growth-inhibiting layer may have a cell size of, for example, 30 to 500 μm, 70 to 400 μm, or 100 to 350 μm. In this range, the bacterial growth-inhibiting layer has a high ability to retain exudate, and thus is effective in maintaining a moist environment.

The wound infection agent-removing layer may have a pore size of for example, 300 μm or less, 0.01 to 200 μm, or 10 to 100 μm. In this range, the wound infection agent-removing layer has the effect of preventing the penetration of newly formed tissue.

The expression "size of pores in the wound infection agent-removing layer is 300 μm or less" may mean that the size of 80% or more, 90% or more or all of pores in the wound infection agent-removing layer is 300 μm or less.

In addition, the wound infection agent-removing layer may have a cell size of, for example, 50 to 400 μm, 70 to 400 μm, or 100 to 350 μm. In this range, the wound infection agent-removing layer has the effect of preventing the penetration of newly formed tissue.

Each of the pore size and the cell size is the mean value obtained by measuring the longest diameter of 7 selected points of a platinum-coated sample by a scanning electron microscope.

The bacterial growth-inhibiting layer and the wound infection agent-removing layer may comprise a foaming mixture of 40 to 70 wt % of a polyurethane prepolymer, 15 to 45 wt % of a foaming agent, 5 to 35 wt % of a crosslinking agent, 0.1 to 2 wt % of a surfactant, and 0.5 to 15 wt % of an adjuvant.

Here, the polyurethane prepolymer is preferably synthesized by reacting 1 to 4 moles of an isocyanate with 0.1 to 2 moles of a polyether polyol.

The isocyanate may be, for example, one or more selected from the group consisting of isophorone diisocyanate, 2,4-toluene diisocyanate, 2,4-toluene diisocyanate isomers, diphenylmethane diisocyanate, hexamethylene diisocyanate, lysine diisocyanate, trimethylhexamethylene diisocyanate, bis(2-isocyanatoethyl)-fumarate, 3,3'-dimethyl-4,4'-diphenylmethane diisocyanate, 1,6-hexane diisocyanate, 4,4'-biphenylene diisocyante, 3,3'-dimethylphenylene diisocyanate, p-phenylene diisocyanate, m-phenylene diisocyanate, 1,5-naphthalene diisocyanate, 1,4-xylene diisocyanate, 1,3-xylene diisocyanate, and the like. Preferably, the isocyanate may be one or more selected from the group consisting of diphenylmethane diisocyanate, 2, 4-toluene diisocyanate, 2,4-toluene diisocyanate isomers, p-phenylene diisocyanate, asoporone diisocyanate, and hexamethylene diisocyanate.

The polyetherpolyol used may be, for example, a 30:70 mixture an ethylene oxide/propylene oxide random copolymer, which has three or more hydroxyl groups in the molecule, a weight-average molecular weight of 3000 to 6000 g/mol and an ethylene oxide content of 50 to 80%, and a polypropylene glycol having two or more hydroxyl groups in the molecule and a weight-average molecular weight of 1000 to 4000 g/mol. Preferably, an ethylene oxide/propylene oxide random copolymer, which has three or more hydroxyl groups in the molecule, a weight-average molecular weight of 3000 to 6000 g/mol and an ethylene oxide content of 50 to 80%, is used alone as the polyetherpolyol. However, a mixture of other isocyanate compound and polyol, which are not mentioned above, may also be used in order to control physical properties.

The foaming agent used may be chlorofluorocarbon (CFC-141b), methylene chloride, or distilled water. Preferably, distilled water is used.

Examples of the crosslinking agent that is used in the present invention include 1,3-butanediol, 1,4-butanediol, 1,5-pentanediol, 1,6-hexanediol, neopentyl glycol, propylene glycol, ethylene glycol, polyethylene glycol (having a weight-average molecular weight of 200 to 2000 g/mol), glycerol, trimethylolethane, trimethyloipropane, pentaerythritol, sorbose, sorbitol, and the like, which have two or more hydroxyl groups in the molecule and may be used alone or in a mixture. Preferably, the crosslinking agent is one or more selected from, the group consisting of glycerol, sorbitol, polyethylene glycol (having a weight-average molecular weight of 200 to 2000 g/mol), and trimethylolpropane.

The surfactant that is used in the present invention may be one or a mixture of two or more selected from among 1-62, L-64, P-84, P-85, P-105, F-68, F-87, F-88, F-108, F-127, and mixtures thereof, which. are ethylene oxide-propylene oxide block copolymers manufactured by BASF (Germany), and. L-508, L-5305, L-5302, and 1-3150, which are silicone-based surfactants manufactured by Osi Co.

The adjuvant may be, for example, one or more selected from the group consisting of a moisturizing agent, a wound healing promoting agent, a pigment, and a cell growth factor.

The moisturizing agent that. is used in the present invention is, for example, one or more selected from the group consisting of polyacrylic acid, polyvinyl alcohol, polyoxyethylene, polyethylene oxide, polysaccharides, polymethacrylic acid, polyacrylamide, polyethylene oxide, cellulose, carboxymethylcellulose, pectin, guar gum, sodium alginate, chitin, chitosan, gelatin, starch, hyaluronic acid, keratin, collagen, dermatan sulfate, pectin, sodium carboxymethylcellulose, locust bean gum, hydroxyethylcellulose, ginseng powder or extracts, vitamins (A, B complex, C, D, B, F, K, U, and P), xanthan gum, pulp, and karaya gum.

The wound healing promoting agent that is used in the present invention is one or more selected from the group consisting of polyacrylic acid, polyvinyl alcohol, polyoxyethylene, polyethylene oxide, polysaccharides, polymethacrylic acid, polyacrylamide, polyethylene oxide, cellulose, carboxymethylcellulose, pectin, guar gum, sodium alginate, chitin, chitosan, gelatin, starch, hyaluronic acid, keratin, collagen, dermatan sulfate, pectin, sodium carboxymethylcellulose, locust bean gum, hydroxyethylcellulose, ginseng powder or extracts, vitamins (A, B complex, C, D, E, F, K, U, and F), xanthan gum, pulp, and karaya gum (the wound healing promoting agent is not the same as the moisturizing agent).

Examples of the cell growth factor include platelet derived growth factor (PDGF), transforming growth factor beta (TGF-β), epidermal growth factor (EGF), fibroblast growth factor (FGF), vascular endothelial growth factor (VEGF) and the like, which may be used alone or in a mixture.

The external infectious agent-blocking layer may be, for example, one or more selected from among nonwoven fabric, a silicone-based film, a polyolefin-based film, and a polyurethane-based film.

In one example, nonwoven fabric may be selected as the external infectious agent-blocking layer. The nonwoven fabric may preferably be a gauze dressing.

In another example, a polyurethane-based film may be selected as the external infectious agent-blocking layer. The polyurethane foam may preferably be a foam dressing.

In one example, the dressing may be formed of the external infectious agent-blocking layer, the bacterial growth-inhibiting layer and the wound infection agent-removing layer, which are disposed sequentially from top to bottom.

In a specific example, the dressing may be formed of the external infectious agent-blocking layer having a thickness of 10 to 500 µm, the bacterial growth-inhibiting layer having a thickness of 0.1 to 20 mm and the wound infection agent-removing layer having a thickness of 0.01 to 100 µm.

In another example, the dressing may be formed of the external infectious agent-blocking layer having a thickness of 10 to 400 µm, the bacterial growth-inhibiting layer having a thickness of 0.1 to 15 mm and the wound infection agent-removing layer having a thickness of 0.1 to 40 µm, which are disposed sequentially from top to bottom.

The dressing may have a density of, for example, 0.05 g/cm$^3$ or higher, or 0.1 to 0.5 g/cm$^3$. In this range, the dressing has excellent adhesion even to the curved surface of the human body.

In a specific example, the dressing of the present invention may comprise a hydrocarbon-based polymer containing a polar group. In this case, the compatibility between the external infectious agent-blocking layer and the wound infection agent-removing layer or between the external inferions agent-blocking layer, the bacterial growth-inhibiting layer and the wound infection agent-removing layer is greatly increased by hydrocarbon chains, and thus the resulting formed article has a stable structure.

The hydrocarbon-based polymer containing a polar group may be, for example, one or more selected from the group consisting or an epoxy-modified polystyrene copolymer, an ethylene-ethylene anhydride-acrylic acid copolymer, an ethylene-ethyl acrylate copolymer, an ethylene-alkyl acrylate-acrylic acid copolymer, a maleic anhydride-modified high-density polyethylene, a maleic anhydride-modified linear low-density polyethylene, an ethylene-alkyl methacrylate-methacrylic acid copolymer, an ethylene-butyl acrylate copolymer, an ethylene-vinyl acetate copolymer, and a maleic anhydride modified ethylene-vinyl acetate copolymer. In this range, compatibility and blocking properties are excellent.

The epoxy-modified polystyrene copolymer may be, for example, a compound comprising 100 parts by weight of a main chin composed of 70 to 99 wt % of styrene and 1 to 30 wt % of an epoxy compound, and 1 to 80 parts by weight of branches composed of acrylic monomers.

Each of the maleic anhydride-modified high-density polyethylene, the maleic anhydride-modified linear low-density polyethylene and the maleic anhydride modified ethylene-vinyl acetate copolymer may comprise 100 parts by weight of a main chain and 0.1 to 10 parts by weight of branches composed of maleic anhydride. In this range, compatibility, ease of operation and commerciality are excellent.

In one example, the hydrocarbon-based polymer containing a polar group may be added in an amount of 0.1 to 10 wt %, or 1 to 5 wt %, based on 100 wt % of the components of each layer of the dressing according to the present invention. In this range, the compatibility between the external infectious agent-blocking layer and the wound infection agent-removing layer or between the external infectious agent-blocking layer, the bacterial growth-inhibiting layer and the wound infection agent-removing layer is greatly increased, and thus the resulting formed article has a stable structure.

According to the present invention, the antibacterial dressing is continuously prepared using a continuous preparation apparatus comprising a laterally movable foaming unit, a cooling unit, a press roller, and a drying unit, which are sequentially disposed in that order.

For example, the continuous preparation apparatus for continuous preparation of the dressing sequentially comprises a laterally movable foaming unit configured to apply a polyurethane prepolymer foaming mixture onto the coating protective film of a first release paper which is being moved by a conveyor, a cooling unit configured to retard curing of the polyurethane prepolymer foaming mixture, a press roller configured to laminate a silicone-coated second release paper on a polyurethane foam that passed through the cooling unit, and a drying unit.

The cooling unit may be selected from, for example, air conditioning devices. Above the laterally movable foaming unit, a polyurethane prepolymer supply unit and a foaming additive supply unit may be disposed. The polyurethane prepolymer foaming mixture and the foaming additives may be supplied to the laterally movable foaming unit by a guide unit, and an air injection nozzle may be provided at the end of the laterally movable foaming unit.

The conveyor may be disposed at an angle of 0° with respect to the horizontal axis of a lower frame, and the roller unit branched from the conveyor so as to supply the second release paper may be disposed tilted at an angle of 15 to 20° with respect to the horizontal axis of the lower frame.

The drying unit may further comprise a unit configured to wind a dressing having a width of 0.1 to 1.1 m and a density of 0.1 to 0.5 g/cm$^3$.

A method for preparing the bacterial growth-inhibiting layer and the wound infection agent-removing layer according to the present invention comprises the steps (i) adding and stirring a polyol and a diol, adding an isocyanate to the stirred polyol and diol to form a mixture, and allowing the mixture to react until a theoretical NCO content (mole %) of 1 to 20 is reached, thereby preparing a polyurethane prepolymer; (ii) adding and uniformly mixing a cell membrane-penetrating component, a crosslinking agent, a foaming agent, a surfactant and an adjuvant, thereby preparing a foaming mixture; (iii) mixing the prepared polyurethane prepolymer and the prepared foaming mixture, and foaming the mixture to form a polyurethane foam while injecting air at a temperature of 1 to 20° C. to retard curing and maintain the viscosity of the polyurethane foam; and (iv) laminating a second release paper on the viscosity-maintained polyurethane foam, following by curing.

The dressing prepared as described above has a two-layer structure which is formed in contact with the first release paper and which is composed of the bacterial growth-inhibiting layer having a thickness of 0.1 to 20 mm and including fine pores having a pore size of 500 μm or less, and the wound infection agent-inhibiting layer having a thickness of 0.01 to 100 μm and including fine pores having a pore size of 300 μm or less.

Hereinafter, preferred examples will be described in order to help understand the present invention. However, these examples are only provided to illustrate the present invention and at will be obvious to those skilled in the art that various alternations and modifications are possible within the scope and technical range of the present invention. Such alternations and modifications fall within the scope of the appended claims.

EXAMPLES

In the following Examples and Comparative Examples, experiments were performed using the following materials.

Synthesis Example 1: Polyurethane Prepolymer

An isocyanate-capped polyurethane prepolymer was prepared in the following manner. 354 g of diphenylmethane diisocyanate and. 314 g of isophorone diisocyanate were introduced into a 3-liter round-bottom flask equipped with a stirrer, and were heated to 80° C. and then reacted until the theoretical NCO content (mole %) reached 3.3, while an ethylene oxide/propylene oxide random copolymer having two or more hydroxyl group was thereto in small amounts. During the reaction, samples were taken and the NCO content (mole %) was measured by a titration method using an n-butylamine standard solution.

Synthesis Example 2: Foaming Mixture

In order to prepare a foaming solution for reaction with the polyurethane prepolymer prepared in Synthesis Example 1, 48.38 wt % of distilled water as a foaming agent, 38.4 wt % of glycerin as a crosslinking agent, 10 wt % Povidone iodine as a rapid cell membrane-penetrating component, 2.8 wt % of F-87 (BASF) as an additive, 0.4 wt % of adjuvant L-64 and 0.02 wt % of a water-soluble pigment were uniformly mixed.

External Infectious Agent-Blocking Layer

To prepare an external infectious agent-blocking layer, 70 parts by weight of methyl ethyl ketone, 25 parts by weight of dimethylformamide and 5 parts by weight of a pigment were added to 100 parts by weight of polyurethane resin. The mixture was stirred, defoamed, applied to a silicone-coated release paper, and then dried, thereby preparing a pore-free, external infectious agent-blocking layer.

Example 1

In a foaming machine having a spray nozzle at the end, Synthesis Example 1 and Synthesis Example 2 were mixed at a weight ratio of 2:1. In the foaming machine, the mixture was stirred at 2,500 rpm for 5 sec, and then the foaming mixture was foamed on the external infectious agent-blocking layer-coated release paper moving on a conveyor at a speed of 5 m/min while air at 20° C. was sprayed thereto to retard curing and maintain the viscosity of the polyurethane foam.

Thereafter, while a roller unit branched from the conveyor was rotated at an angle of 15 to 20° with respect to the horizontal axis of the lower frame such that a silicone-coated second release paper was supplied on the polyurethane foam, the polyurethane foam was passed through a chamber such that it was laminated with the silicone-coated second release paper. Next, the resulting material was cured in a drying unit at 30° C. for 1 minute, thereby obtaining a sheet-like rolled dressing comprising a 5 nm-thick bacterial growth inhibiting layer and a wound infection agent-removing layer.

The dressing was composed of a 25 μm-thick external infectious agent-blocking layer, a 25 μm-thick wound infection agent-removing layer containing the rapid cell membrane-penetrating component, and a 5 mm-thick bacterial growth-inhibiting layer containing the rapid cell membrane-penetrating component.

Comparative Example 1

Allevyn Ag foam dressing (Smith & Nephew).

Comparative Example 2

Mepilex Ag foam dressing (Molnlycke Health Care).

Comparative Example 3

Acticoat dressing (Smith & Nephew).

Comparative Example 4

Aguacel Ag dressing (Convatec).

The physical properties of the polyurethane foam dressings obtained in Example 1 and Comparative Examples 1 to 4 were measured in the following manner.

Morphology Measurement

Surface analysis of the wound infection agent-removing layer and bacterial growth-inhibiting layer of each of Example and Comparative Examples 1 to 4 was performed using a scanning electron microscope (SHIMADZU Co., Ltd., SUPERSCANSS-550).

The wound infection agent-removing layer in each of Example 1 and Comparative Examples 1 to 4 was coated with platinum ions, and then the surface was observed with a scanning electron microscope (SHIMADZU Co., Ltd., SUPERSCANSS-550). The results of the observation are shown in FIG. 1, and the pore size of the layer is shown in Table 1 below.

The bacterial growth-inhibiting layer in each of Example 1 and Comparative Examples 1 to 4 was coated with platinum ions, and then the surface was observed with a scanning electron microscope (SHIMADZU Co., Ltd., SUPERSCANSS-550). The results of the observation are shown in FIG. 1, and the pore size of the layer is shown in Table 2 below.

Figure 1:
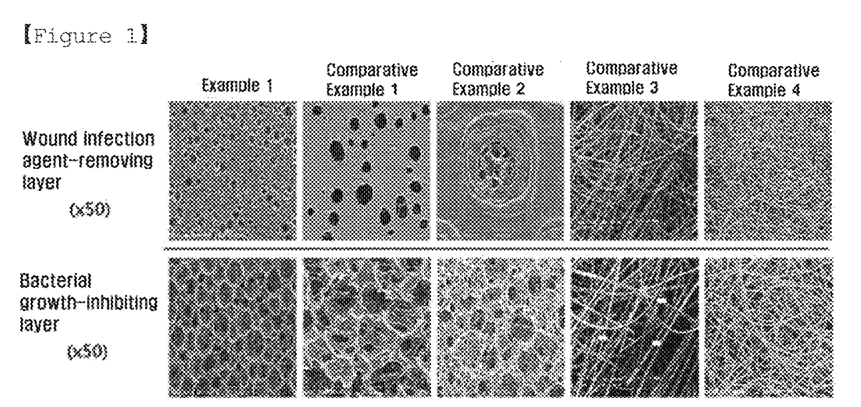
FIG. 1 shows the results of observing a wound infection agent-removing layer and a bacterial growth-inhibiting layer with a scanning electron microscope in Example 1 and Comparative Examples 1 to 4.

As shown in FIG. 1, in Example 1 according to the present invention, the wound infection agent-removal layer had a pore size such that newly formed tissue could not penetrate the layer, and the pore size of the bacterial growth-inhibiting layer was also small, suggesting that Example 1 has a high ability to retain exudate and to maintain a moist environment. However, the dressings of Comparative Examples 1 and 2 had a disadvantage in that, because the pore size was large, newly formed tissue could easily penetrate the dressings such that the dressings could adhere to wounds. Furthermore, the dressings of Comparative Examples 3 and 4 had a fibrous structure difficult to have a suitable ability to retain exudate.

TABLE 1

| | Pore size (μm) of would infection agent-removing layer | | | | | | | Pore size range |
|---|---|---|---|---|---|---|---|---|
| | 1 | 2 | 3 | 4 | 5 | 6 | 7 | |
| Example 1 | 33 | 66 | 25 | 45 | 56 | 62 | 72 | 25 to 75 |
| Comparative Example 1 | 55 | 258 | 343 | | | | | 55 to 343 |
| Comparative Example 2 | 67 | 92 | 113 | 154 | 98 | 132 | 116 | 52 to 154 |

TABLE 2

| | Pore size (μm) of bacterial growth-inhibiting layer | | | | | | | Pore size range |
|---|---|---|---|---|---|---|---|---|
| | 1 | 2 | 3 | 4 | 5 | 6 | 7 | |
| Example 1 | 132 | 169 | 298 | 150 | 350 | 136 | 100 | 100 to 350 |
| Comparative Example 1 | 462 | 346 | 581 | 645 | 643 | 607 | 597 | 346 to 645 |
| Comparative Example 2 | 399 | 345 | 169 | 453 | 409 | 412 | 455 | 169 to 455 |

Measurement of Absorption and Retaining Capacities

Figure 2:
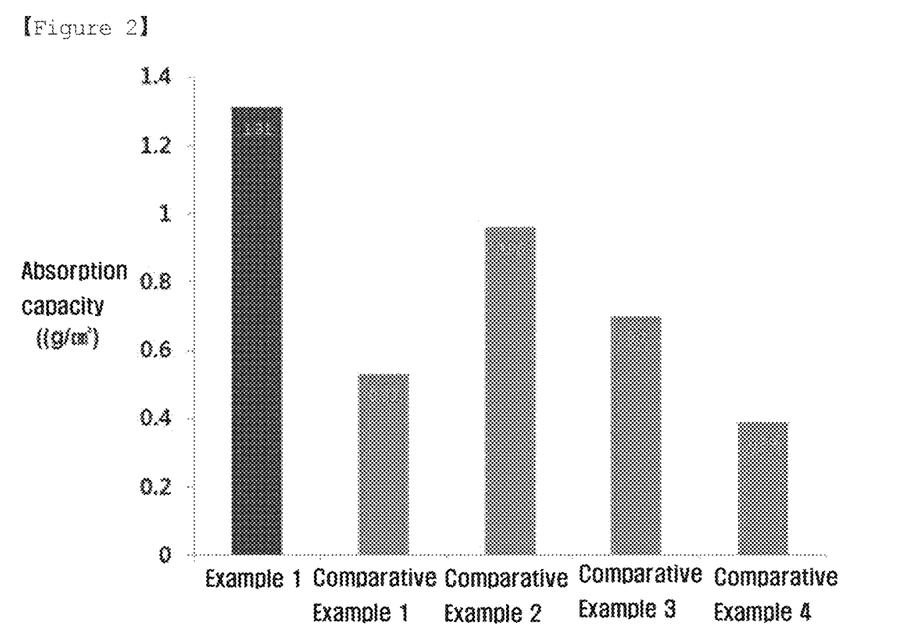
FIG. 2 is a graph showing the results of measuring the absorption ability of dressings of Example 1 and Comparative Examples 1 to 4.

To measure absorption capacity, the dressing of each of Example 1 and Comparative Examples 1 to 4 was cut to a size of 5 cm×5 cm, and dried in a vacuum oven at 50° C. for 24 hours, and then the initial weight (WI) thereof was measured. Next, each dressing sample was immersed in distilled water at 37° C. for 30 minutes, and then water was removed from each dressing sample, and the weight (W2) of each dressing sample was measured. The absorption capacity of each dressing sample was calculated using the following equation 1, and the results of the calculation are shown in FIG. 2

$$\text{Absorption capacity (g/cm}^2\text{)}=(W2-W1)g/\text{initial sample area (cm}^2\text{)} \quad \text{Equation 1}$$

Figure 3:
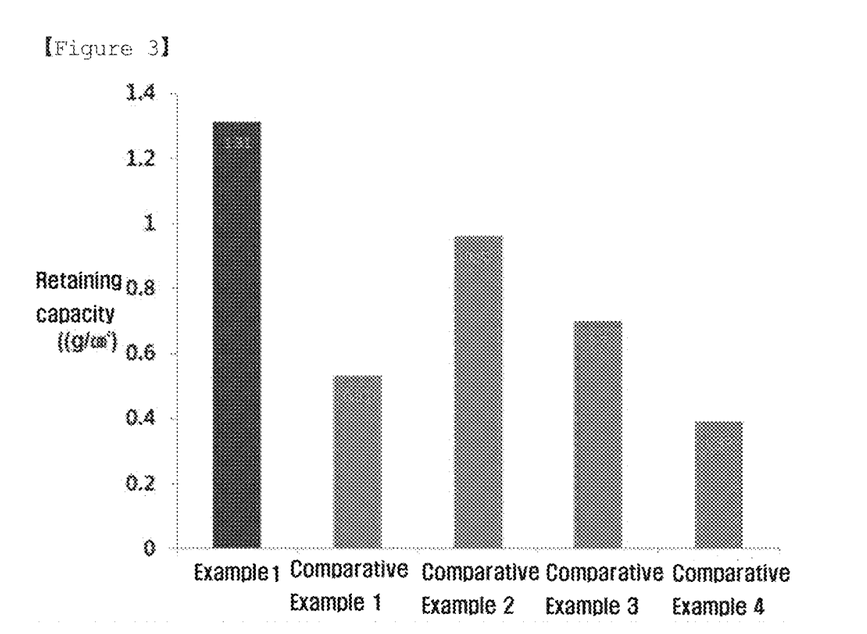
FIG. 3 is a graph showing the results of measuring the retaining ability of dressings o Example 1 and Comparative Examples 1 to 4.

To measure retaining capacity, each sample whose absorption capacity was measured was pressed with a 5 kg weight for 20 seconds, and then the weight (W3) of each sample was measured. The retaining capacity of each sample was calculated using the following equation 2, and the results of the calculation are shown in FIG. 3.

$$\text{Retaining capacity (g/cm}^2\text{)}=(W3-W1)g/\text{initial sample area (cm}^2\text{)} \quad \text{Equation 2}$$

Example 1 has a better ability to absorb exudate than Comparative Examples 1 to 4, and thus has the effect of inducing rapid wound healing. In addition, Example 1 has an excellent ability to retain exudate, and thus has the effect of preventing maceration.

Cytotoxicity Measurement

In accordance with ISO 10993-5, 12, cells monolayer-cultured with MEM medium were trypsinized and adjusted to a cell concentration of $10^5$ cells/ml, and 100 μm of the trypsinized cell suspension were added to each well of a 96-well plate. The trypsinized cells were cultured (37° C. and 5% $CO_2$) for 24 hours, and the monolayer-cultured wells were selected and designated as Example 1 and Comparative Examples 1 to 4, respectively, and then the medium was removed.

Figure 4:
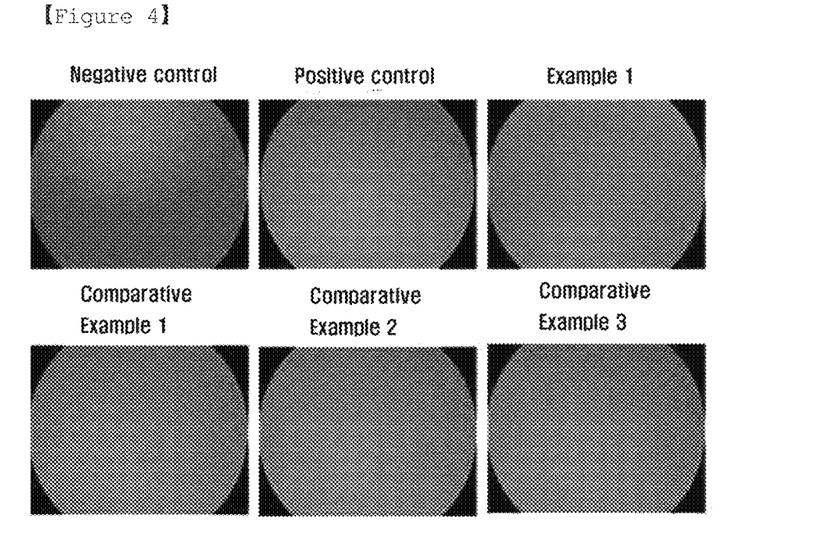

Next, 100 μl of each of Example 1, Comparative Example 1 to 3 and control extracts was added to the selected wells and incubated in a 5% $CO_2$ incubator at 37° C. for 24 hours. After completion of the incubation, lysis or morphology of the cells was observed with a microscope (40×), and the results of the observation are shown in FIG. 4. In addition, cell viability was measured by an MIT assay, and the results of the measurement are shown in FIG. 5.

Figure 5:
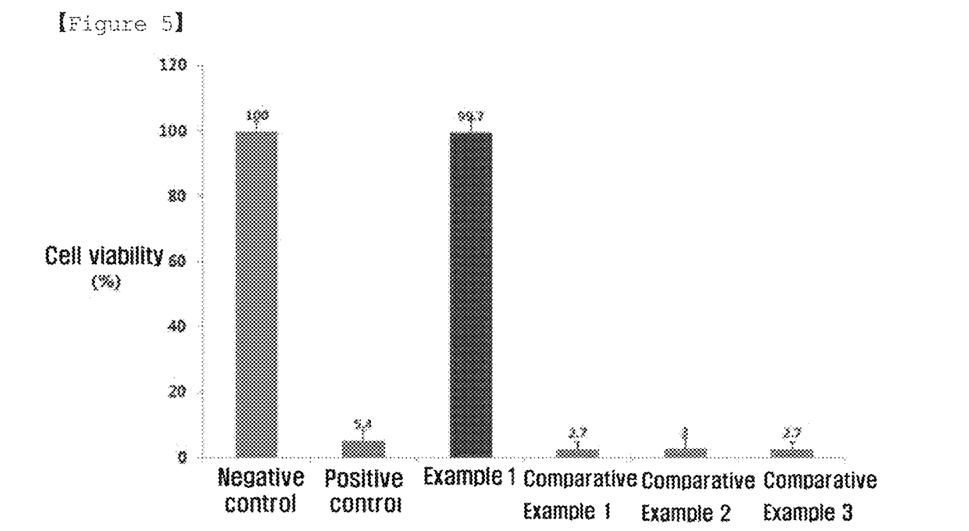
FIG. 5 is a graph showing the results of measuring cell viability for Example 1 and Comparative Examples 1 to 3.

In FIG. 5, the negative control shows cell proliferation without cytotoxicity, and the positive control shows a state with cytotoxicity. As can be seen in FIG. 5, Example 1 showed cell proliferation, similar to the negative control, but Comparative Examples 1 to 3 were cytotoxic, similar to the positive control.

From the cytotoxicity test, it could be seen that cell viability in Example 1 was significantly higher than that in Comparative Examples 1 to 3.

Measurement of Antibacterial Activity

Figure 6:
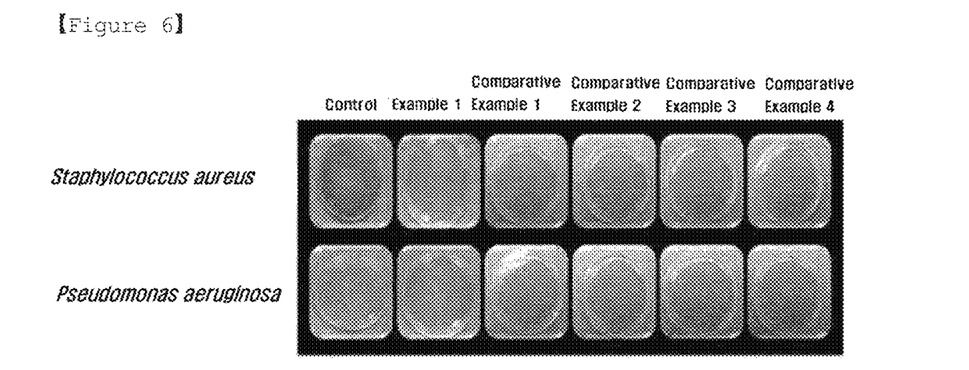
FIG. 6 depicts photographs showing the results of antibacterial activity tests for Example 1 and Comparative Examples 1 to 4.
Figure 7:
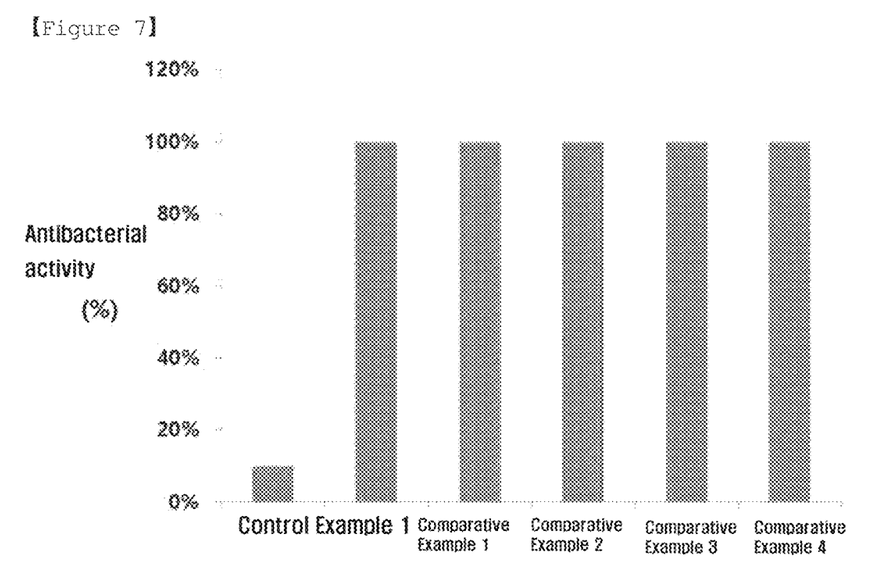
FIG. 7 is a graph showing the results of measuring the antibacterial activity of Example 1 and Comparative Examples 1 to 4.

In accordance with ASTM E2149-10, each of the samples of Example 1 and Comparative Examples 1 to 4 was prepared in an amount of 1.0±0.1 g, and then a 250-ml sterile shake flask was prepared for each sample, and 50±0.5 ml of a dilution of bacterial inoculum was added to each flask. Each of the samples of Example 1 and Comparative Examples 1 to 4 was placed an each flask, and then each flask was placed on a wrist-action shaker and shaken at the maximum speed for 60±5 min to dilute each sample. Next, each dilution was added to a plate medium and incubated in an incubator at 35±2° C. for 24 hours, and then the number of colonies in the petri dish was observed with a microscope. The micrographs are shown in FIG. 6, and antibacterial activity calculated using the following equation is shown in FIG. 7.

$$\text{Antibacterial activity (\%)}=(B-A)/B*100 \qquad \text{Equation 3}$$

A. number of bacterial colonies after contact between sample and bacterial dilution;

B: number of bacterial colonies in control not treated with sample.

As can be seen in the micrographs of FIG. 6, Example 1 and Comparative Examples 1 to 4 did not show *Staphylococcus aureus* and *Pseudomonas aeruginosa*.

In addition, as can be seen. in FIG. 7, Example 1 and Comparative Examples 1 to 1 showed an antibacterial activity of 99% or more.

Thus, it was shown that Example 1 was not cytotoxic and, at the same time, had better antibacterial activity than Comparative Examples 1 to 4.

Measurement of Time-Dependent Antibacterial Activity

In accordance with ASTM E2149-10, each of the samples of Example 1 and Comparative Examples 1 to 4 was prepared in an amount of 1.0±0.1 g, and then a 250-ml sterile shake flask was prepared for each sample, and 50±0.5 ml of a dilution of bacterial inoculum was added to each flask. Each of the samples of Example 1 and Comparative Examples 1 to 4 was placed in each flask, and then each flask was placed on a wrist-action shaker and shaken at the maximum speed for 60±5 min. During contact between each sample and the dilution of bacterial inoculum in the shaker, sampling was done at various time points (1 min, 5 min, 10 min, 20 min, 30 min and 60 min). All the samples were immediately serially diluted, and the dilutions were added to plate media and incubated in an incubator at 35±2° C. for 24 hours, after which the number of colonies in the incubation petri dish was observed with a microscope. The micrographs are shown in FIG. 8 for *Staphylococcus aureus* and in FIG. 9 for *Pseudomonas aeruginosa*.

Figure 8:
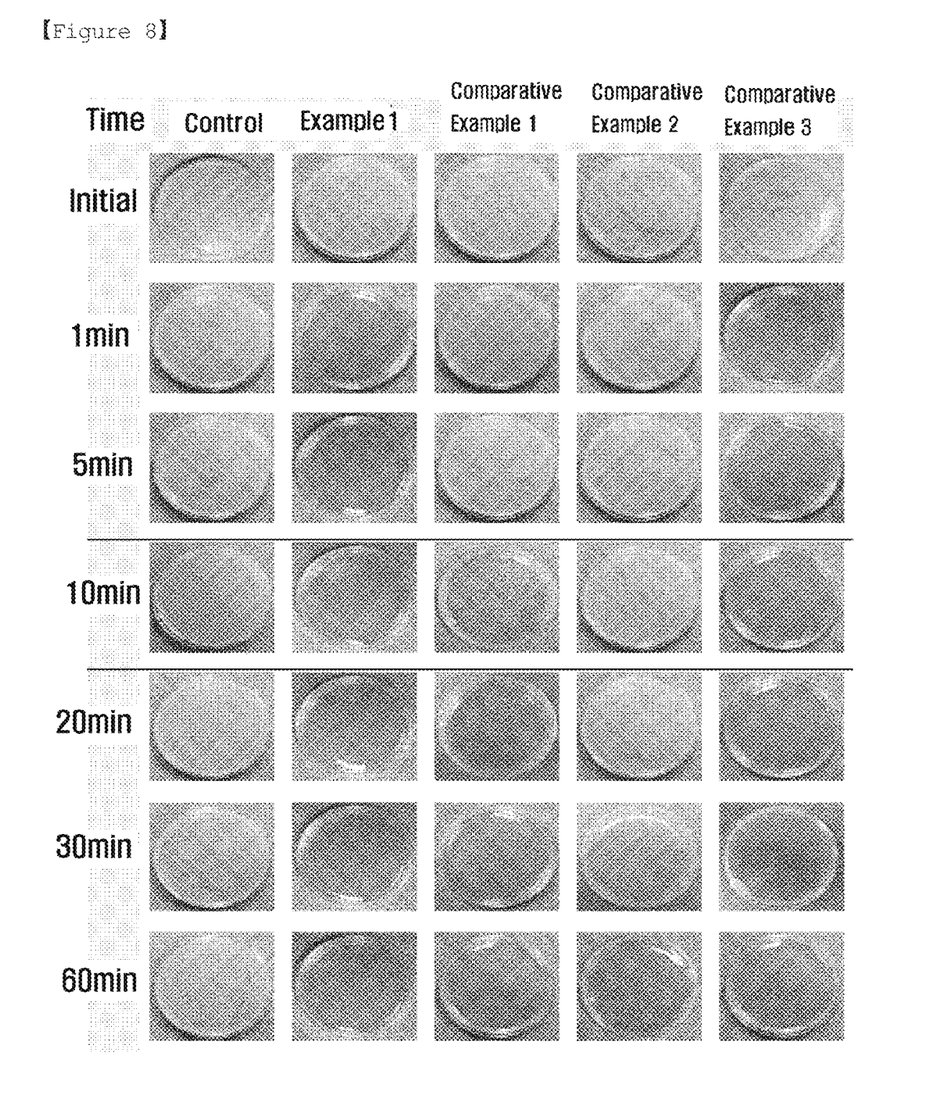
FIG. 8 depicts photographs showing the results of testing the time-dependent antibacterial activity of Example 1 and Comparative Examples 1 to 3 against *Staphylococcus aureus*.
Figure 9:
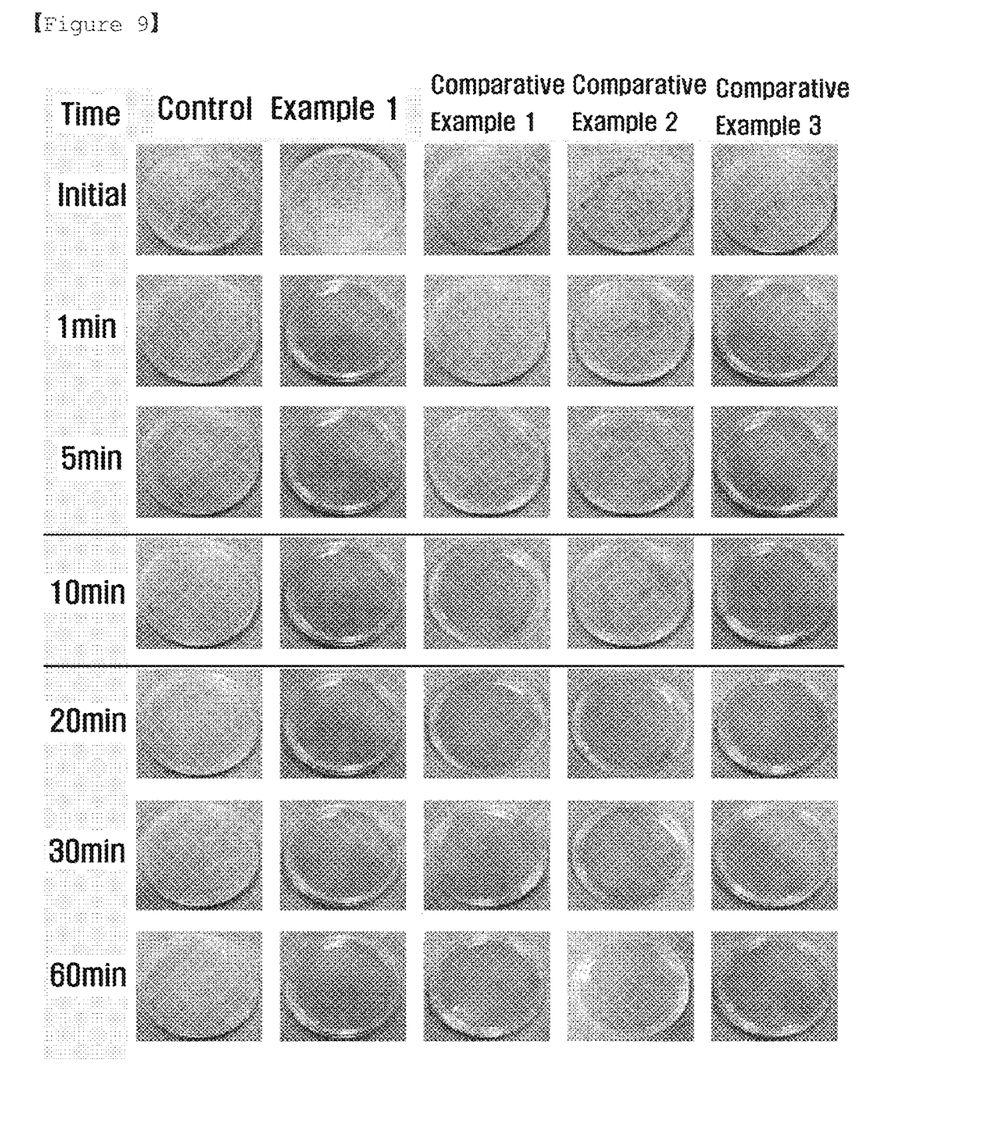
FIG. 9 depicts photographs showing the results of testing the time-dependent antibacterial activity of Example 1 and Comparative Examples 1 to 3 against *Pseudomonas aeruginosa*.

As can be seen in the micrographs of FIGS. 8 and 9, *Staphylococcus aureus* and *Pseudomonas aeruginosa* did not appear in Example 1 and Comparative Example 3 within a contact time of 1 min. However, these bacteria did not appear in Comparative Example 1 at a contact time of 30 min more and in Comparative Example 2 at a contact time of 60 min or more.

Thus, it was shown that Example 1 showed antibacterial activity from a shorter time than Comparative Examples 1 and 2.

Measurement of Animal Skin Regeneration Effectiveness

Figure 10:
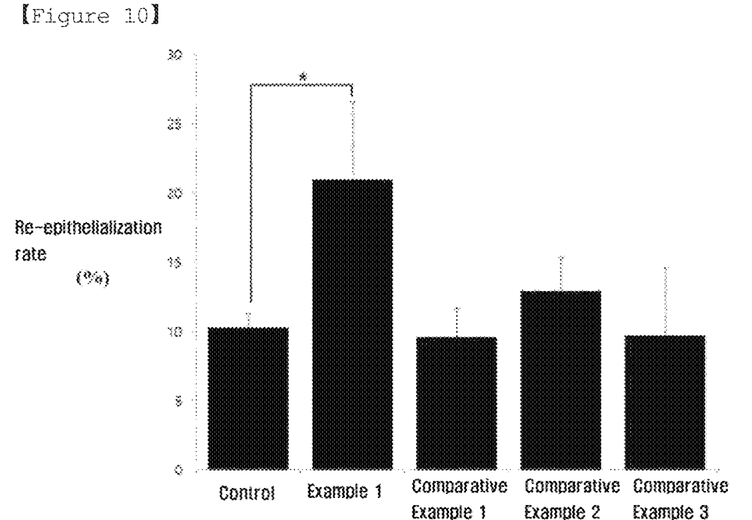
FIG. 10 is a graph showing the results of measuring re-epithelialization rate in the measurement of animal skin regeneration effectiveness or Example 1 and Comparative Examples 1 to 3.
Figure 11:
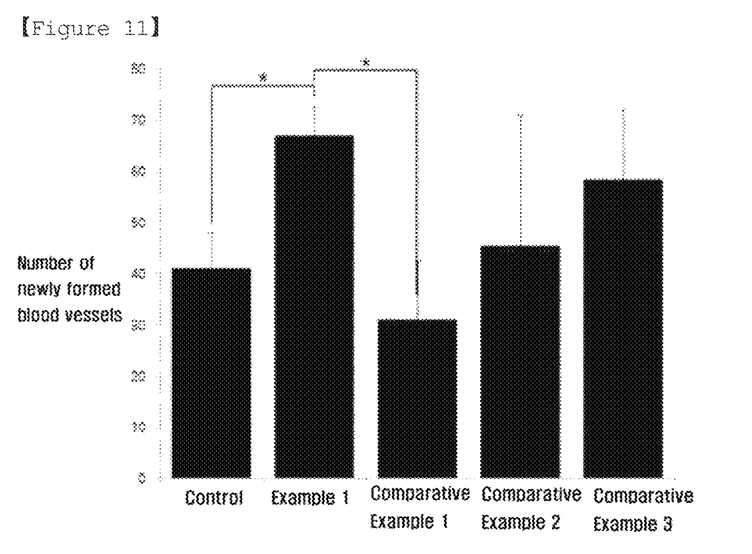
FIG. 11 is a graph showing the results of measuring the number of newly formed blood vessels in the measurement of animal skin regeneration effectiveness of Example 1 and Comparative Examples 1 to 3.
Figure 12:
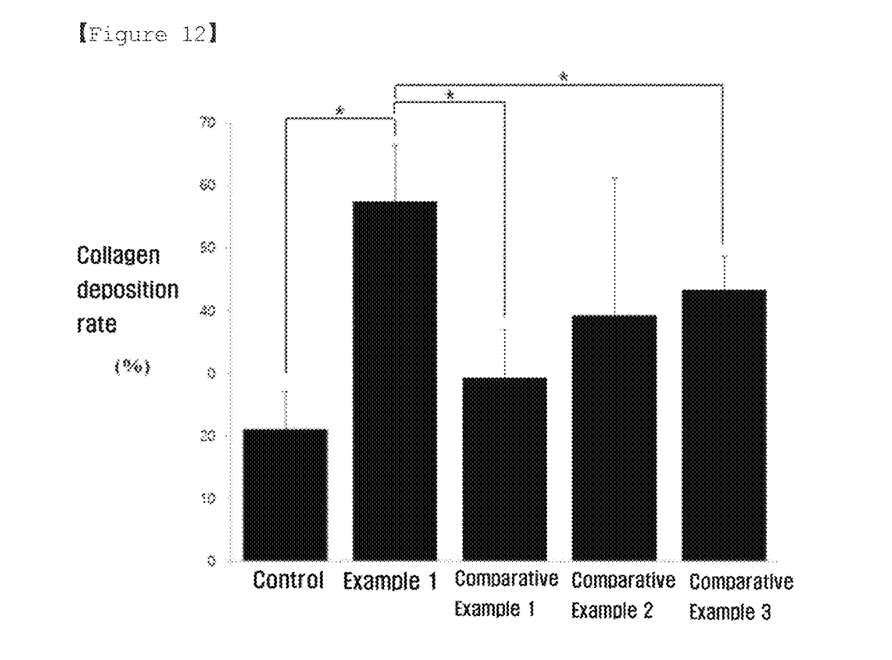
FIG. 12 is a graph showing the results of measuring collagen deposition rate in the measurement of animal skin regeneration effectiveness of Example 1 and Comparative Examples 1 to 3.

The entire back of SD (Sprague Dawley) rats was shaved, and up to fascia lavers in the center of the back were removed to induce a 2.5 cm² wound. To prevent wound contraction, wound edges were sutured with a suture using a silicone ring, and then each of a control (gauze), Example 1 and Comparative Examples 1 to 3 was applied to the wound, wrapped once with a self-adhesive bandage, and fixed with a sticking plaster. At 3-day intervals, the control, Examples 1, Comparative Examples 1 to 3 and the self-adhesive bandage were replaced. On day 14, the animals of each group were sacrificed, and regenerated tissue was collected and subjected to tissue staining. Re-epithelialization rate is shown in FIG. 10, and the number of newly formed blood vessels is shown in FIG. 11. Moreover, collagen deposition rate is shown in FIG. 12.

The re-epithelialization rate was calculated using the following equation 4:

$$\text{Re-epithelialization rate (\%)}=\text{re-epithelialized length/initial wound length}*100 \qquad \text{Equation 4}$$

The newly formed blood vessel number was measured by directly counting the blood vessel. number of re-epithelialized tissue in a wound area of 2.5 cm².

The collagen deposition rate was measured by performing special staining of dermal connective tissue collagen by Masson's trichrome staining, and measuring the area of collagen relative to the total area of three positions of the dermal layer by use of image J program according to the following equation 5:

$$\text{Collagen deposition rate (\%)}=\text{collagen area of dermal layer/total area of dermal layer}*100 \qquad \text{Equation 5}$$

As can be seen in FIG. 10, the re-epithelialization rate was the highest in Example 1 than in the control and Comparative Examples 1 to 3. As can be seen in FIGS. 11 and 12, the number of newly formed blood vessels was the largest in Example 1 than in the control and Comparative Examples 1 to 3, and Example 1 showed the highest collagen deposition rate.

Thus, it could be seen that Example 1 shows higher re-epithelialization rate, new blood vessel formation and collagen deposition rate compared to Comparative Examples 1 to 3, suggesting that Example 1 has excellent animal skin regeneration effectiveness.

The invention claimed is:

1. An antibacterial dressing comprising: an external infectious agent-blocking film layer; a bacterial growth-inhibiting polyurethane foam layer; and a wound infection agent-removing polyurethane foam layer,
   wherein the bacterial growth-inhibiting polyurethane foam layer contains a rapid cell membrane-penetrating component and has a pore size of 100 to 350 μm together with a cell size of 100 to 350 μm, and the wound infection agent-removing polyurethane foam layer contains a rapid cell membrane-penetrating component and has a pore size of 25 to 75 μm together with a cell size of 100 to 350 μm to prevent reinfection by absorbing and destroying bacteria in the bacterial growth-inhibiting polyurethane foam layer, and then to prevent bacteria from returning to the wound infection agent-removing polyurethane foam layer.

2. The antibacterial dressing of claim 1, wherein the rapid cell membrane-penetrating component comprises one or more selected from among potassium iodate, potassium biiodate, methyl iodide, hydroiodic acid, acetyl iodide, and Povidone iodine.

3. The antibacterial dressing of claim 1, wherein the antibacterial dressing has an antibacterial activity of 90% or more as measured in accordance with ASTM E2149-10.

4. The antibacterial dressing of claim 1, wherein the antibacterial dressing has an absorption capacity of 1.0 g/cm² or more as calculated using the following equation 1:

Absorption capacity (g/cm²)=(W2−W1)g/initial sample area (cm²)   Equation 1 wherein W1 is an initial weight of the dressing, measured after cutting the dressing to a size of 5 cm×5 cm and drying the cut dressing in a vacuum oven at 50° C. for 24 hours, and W2 is a weight of the dressing, measured after immersing the dressing in distilled water at 37° C. for 30 minutes and then removing water from the surface of the dressing.

5. The antibacterial dressing of claim 1, wherein the antibacterial dressing has a retaining capacity of 0.2 g/cm² or more as calculated using the following equation 2:

Retaining capacity (g/cm²)=(W3−W1)g/initial sample area (cm²)   Equation 2 wherein W1 is an initial weight of the dressing, measured after cutting the dressing to a size of 5 cm×5 cm and drying the cut dressing in a vacuum oven at 50° C. for 24 hours, and W3 is a weight of the dressing, measured after immersing the dressing in distilled water at 37° C. for 30 minutes, and then removing water from the surface of the dressing and pressing the dressing with a 5 kg weight for 20 minutes.

6. The antibacterial dressing of claim 1, wherein the antibacterial dressing shows a re-epithelialization rate of 15% or more as calculated using the following equation 4, and shows an excellent skin regeneration effect in this range:

Re-epithelialization rate (%)=re-epithelialized length/initial wound length*100   Equation 4 wherein the re-epithelialized length and the initial wound length are measured by shaving an entire back of an SD (Sprague Dawley) rat, removing up to fascia layers in the center of the back to induce a 2.5 cm² wound, suturing wound edges with a suture using a silicone ring in order to prevent wound contraction, applying the dressing to the wound, wrapping the dressing once with a self-adhesive bandage, fixing it with a sticking plaster, replacing the bandage at 3-day intervals, sacrificing the animal on day 14, collecting regenerated tissue, and performing tissue staining.

7. The antibacterial dressing of claim 1, wherein the antibacterial dressing shows a newly formed blood vessel number of 60/2.5 cm² or more, wherein the newly formed blood vessel number is measured by shaving an entire back of an SD (Sprague Dawley) rat, removing up to fascia layers in the center of the back to induce a 2.5 cm² wound, suturing wound edges with a suture using a silicone ring in order to prevent window shrinkage, applying the dressing to the wound, wrapping the dressing once with a self-adhesive bandage, fixing it with a sticking plaster, replacing the bandage at 3-day intervals, sacrificing the animal on day 14, collecting regenerated tissue, performing tissue staining, and directly counting the blood vessel number of re-epithelialized tissue in a wound area of 2.5 cm².

8. The antibacterial dressing of claim 1, wherein the antibacterial dressing shows a collagen deposition rate of 45% or more as calculated using the following equation 5:

Collagen deposition rate (%)=collagen area of dermal layer/total area of dermal layer*100   Equation 5 wherein the collagen deposition rate is measured by shaving the entire back of an SD (Sprague Dawley) rat, removing up to fascia layers in the center of the back to induce a 2.5 cm² wound, suturing the wound edges with a suture using a silicone ring in order to prevent window shrinkage, applying the dressing to the wound, wrapping the wound once with a self-adhesive bandage, fixing it with a bandage, replacing the bandage at 3-day intervals, sacrificing the animal on day 14, collecting regenerated tissue, performing special staining of dermal connective tissue collagen by Masson's trichrome staining, and measuring the area of collagen relative to the total area of three positions of the dermal layer by use of Image J program.

9. The antibacterial dressing of claim 2, wherein the rapid cell membrane-penetrating component is a substance represented by the following formula 1:

wherein n is an integer ranging from 1 to 100, m is an integer ranging from 1 to 2000, and n:m is 1:10 to 1:25.

10. The antibacterial dressing of claim 1, wherein the bacterial growth-inhibiting polyurethane foam layer and the wound infection agent-removing polyurethane foam layer comprise a foaming mixture of 40 to 70 wt % of a polyurethane prepolymer, 15 to 45 wt % of a foaming agent, 5 to 35 wt % of a crosslinking agent, 0.1 to 2 wt % of a surfactant, and 0.5 to 15 wt % of an adjuvant.

11. The antibacterial dressing of claim 10, wherein the polyurethane prepolymer has a 3,3 of NCO index calculated from ratio of [NCO]/[OH].

12. The antibacterial dressing of claim 1, wherein the dressing agent comprises the external infectious agent-blocking film layer having a thickness of 10 to 500 μm, the bacterial growth-inhibiting polyurethane foam layer having a thickness of 0.1 to 20 mm and the wound infection agent-removing polyurethane foam layer having a thickness of 0.01 to 100 μm, which are disposed sequentially from top to bottom.

13. The antibacterial dressing of claim 1, wherein the bacterial growth-inhibiting polyurethane foam layer and the wound infection agent-removing polyurethane foam layer contains the rapid cell membrane-penetrating component in an amount of 0.01 to 10 wt % based on 100 wt % of the bacterial growth-inhibiting polyurethane foam layer and the wound infection agent-removing polyurethane foam layer, respectively.

14. The antibacterial dressing of claim 1, wherein the external infectious agent-blocking film layer is one or more selected from the group consisting of nonwoven fabric, a silicone-based film, a polyolefin-based film, and a polyurethane-based film.

15. An apparatus for continuously preparing the antibacterial dressing of claim 1, the apparatus comprising a laterally movable foaming unit, a cooling unit, a press roller, and a drying unit, which are disposed sequentially in that order.

16. A method for preparing the antibacterial dressing of claim 1, wherein the bacterial growth-inhibiting layer and the wound infection agent-removing layer are prepared by a method comprising the steps of:
(i) adding and stirring a polyol and a diol, adding an isocyanate to the stirred polyol and diol to form a mixture, and allowing the mixture to react under a nitrogen atmosphere until a theoretical NCO content (mole %) of 1 to 20 is reached, thereby preparing a polyurethane prepolymer; (ii) adding and uniformly mixing a cell membrane-penetrating component, a crosslinking agent, a foaming agent, a surfactant and an adjuvant, thereby preparing a foaming mixture; (iii) mixing the prepared polyurethane prepolymer and the prepared foaming mixture, and foaming the resulting mixture to form a polyurethane foam while injecting air at a temperature of 1 to 20° C. to retard curing and maintain a viscosity of the polyurethane foam; and (iv) laminating a second release paper on the viscosity-maintained polyurethane foam, following by curing.

\* \* \* \* \*